(12) United States Patent
Tsujii et al.

(10) Patent No.: US 6,180,652 B1
(45) Date of Patent: Jan. 30, 2001

(54) SULFOXIDE COMPOUNDS AND ACETONE COMPLEXES, AND A PROCESS FOR PRODUCING THE SAME

(75) Inventors: Masahiko Tsujii; Nobuo Niikawa, both of Chiba; Keizo Takayanagi, Ibaraki; Shigeharu Nochi, Tokyo, all of (JP)

(73) Assignee: Eisai Co., Ltd., Tokyo (JP)

( * ) Notice: Under 35 U.S.C. 154(b), the term of this patent shall be extended for 0 days.

(21) Appl. No.: 09/433,786

(22) Filed: Nov. 3, 1999

(30) Foreign Application Priority Data

Nov. 16, 1998 (JP) .................................................. 10-325661

(51) Int. Cl.$^7$ .......................... A61K 31/44; C07D 211/20
(52) U.S. Cl. ......................................... 514/338; 546/273.7
(58) Field of Search .............................. 546/273.4, 273.7; 514/338

(56) References Cited

U.S. PATENT DOCUMENTS

| | | | |
|---|---|---|---|
| 3,853,850 | * 12/1974 | Wilson et al. ..................... | 260/239.1 |
| 4,255,431 | 3/1981 | Junggren et al. . | |
| 4,628,098 | 12/1986 | Nohara et al. . | |
| 4,758,579 | 9/1988 | Kohl et al. . | |
| 5,045,552 | 9/1991 | Souda et al. . | |

FOREIGN PATENT DOCUMENTS

| | | | |
|---|---|---|---|
| 0005129 | 10/1979 | (EP) . | |
| 54-141783 | 11/1979 | (JP) . | |
| 61-22079 | 1/1986 | (JP) . | |
| 61-50978 | 3/1986 | (JP) . | |
| 64-6270 | 1/1989 | (JP) . | |
| WO 96/01623 | * 1/1996 | (WO) ............................... | A61K/9/26 |
| 9821201 | 5/1998 | (WO) . | |
| 9828294 | 7/1998 | (WO) . | |

* cited by examiner

*Primary Examiner*—John Kight
*Assistant Examiner*—Binta Robinson
(74) *Attorney, Agent, or Firm*—Birch, Stewart, Kolasch & Birch, LLP

(57) ABSTRACT

The present invention provides acetone complexes of sulfoxide compounds, useful as medicines such as inhibitors of gastric acid secretion and anti-ulcer agents or as intermediates for production of medicines, a process for producing the same and a purification method of using the same.

Namely, it is the acetone complexes of sulfoxide compounds or of pharmaceutically acceptable salts thereof represented by the following formula:

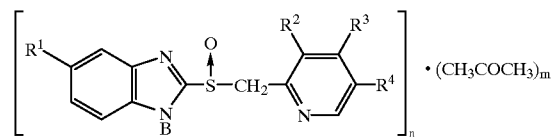

(I)

(wherein $R^1$ represents a hydrogen atom, a methoxy group or a difluoromethoxy group, $R^2$ represents a methyl group or a methoxy group, $R^3$ represents a 3-methoxypropoxy group, a methoxy group or a 2,2,2-trifluoroethoxy group, $R^4$ represents a hydrogen atom or a methyl group, n and m independently represent an integer of 1 to 4, and B represents a hydrogen atom, an alkali metal atom or ½ alkaline earth metal atom), which are obtained by treating the sulfoxide compounds or pharmaceutically acceptable salts thereof with acetone.

9 Claims, No Drawings

SULFOXIDE COMPOUNDS AND ACETONE COMPLEXES, AND A PROCESS FOR PRODUCING THE SAME

FIELD OF THE INVENTION

The present invention relates to a novel acetone complex of a sulfoxide compound or of a pharmacologically acceptable salt thereof useful as medicines such as inhibitors of gastric acid secretion and anti-ulcer agents or as intermediates for production of medicines, as described in JP-A 1-6270 (Example 32), JP-A 61-50978 (Example 2), JP-A 54-141783 (Example 21) or JP-A 61-22079 (Example 2), a process for producing the same and a purification method using the same.

PRIOR ART

Heretofore, sulfoxide compounds have been prepared by oxidizing thioether compounds with an oxidizing agent such as hydrogen peroxide, m-chloroperbonzoic acid, sodium hypochlorite, sodium hypobromite etc., as described in JP-A 1-6270 (EP 268956, U.S. Pat. No. 5,045,552), JP-A 61-50978 (EP 174726, U.S. Pat No. 4,628,098), JP-A 54-141783 (EP 5129, U.S. Pat. No. 4,255,431), JP-A 61-22079 (EP 166287, U.S. Pat. No. 4,758,579) etc.

(See the following reaction scheme wherein $R^1$ to $R^4$ have the same meanings as defined below.)

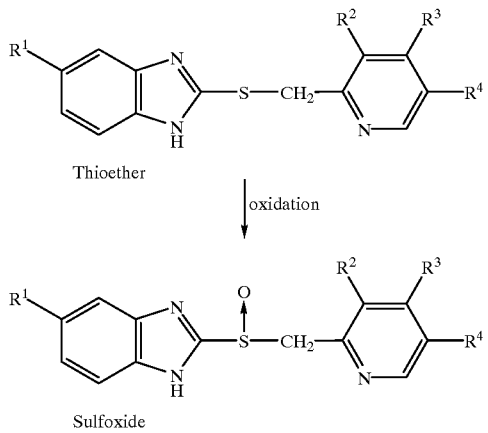

Among the oxidizing agents described above, m-chloroperbenzoic acid is frequently used from the viewpoint of easiness of weighing, storage stability, reaction activity etc.

For example, in Example 32 of JP-A 1-6270, thioether is oxidized with 0.96 equivalent (in terms of the amount of a purified product) of m-chloroperbenzoic acid, but in some cases, the reaction does not stop at the stage of sulfoxide, so there is the problem of the side reaction of further oxidation of a part of the formed sulfoxide into sulfone, as shown in the following reaction. As a matter of course, formation of the sulfone brings about the drawback of lower yield of the desired sulfoxide, and another problem is that it is difficult to separate and purify the 2 compounds because of their very similar physicochemical properties.

(In the following reaction, $R^1$ to $R^4$ have the same meanings as defined above.)

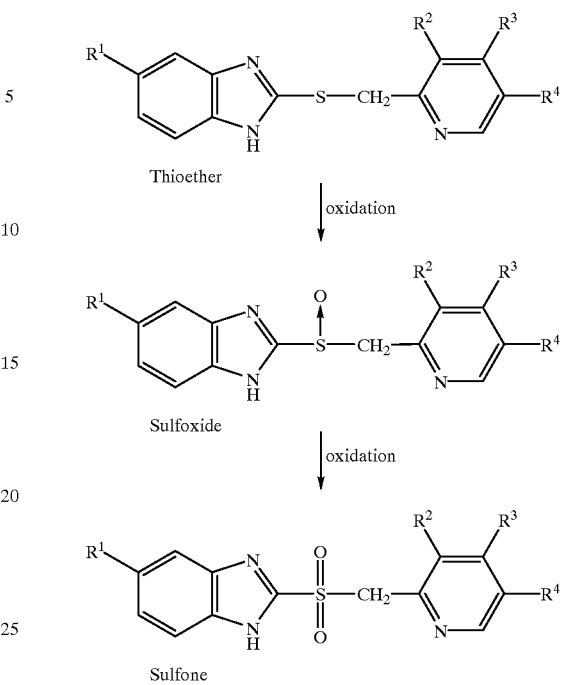

Further, many sulfoxide compounds or their pharmacologically acceptable salt (III) are unstable to air, humidity, heat, light, pH etc., and their decomposition reaction occurs during purification procedures in conventional purification methods such as column chromatography etc., so there is the problem that the purity of their product can be lowered on the contrary. Further, during storage as raw material (bulk), they may also be partially decomposed to lower their purity, but no method for stable storage thereof for a prolonged period of time has been established.

Under the present circumstances as described above, there are no established methods for purifying and stabilizing industrially superior high-purity sulfoxide compounds or their pharmaceutically acceptable salts (III), so there is a need for new superior purification and stabilization methods.

DISCLOSURE OF THE INVENTION

The present inventors made extensive study to solve the problems described above. As a result, they have unexpectedly found the novel acetone complexes described below and that by using these complexes, the objective sulfoxide compounds or their pharmacologically acceptable salts (III) can be purified in high yield and high purity and further they can be stored as raw material (bulk) stably for a prolonged period of time, to arrive at completion of the present invention.

Accordingly, the present invention is to provide novel acetone complexes (I) of sulfoxide compounds or of their pharmacologically acceptable salts (III) useful as medicines such as inhibitors of gastric acid secretion and anti-ulcer agents or as intermediates for production of medicines, a purification method using the same and a method capable of storing sulfoxides or their pharmacologically acceptable salts (III) stably for a prolonged period of time.

Hereinafter, the present invention is described in detail.

First, the acetone complex (I) of a sulfoxide compound or of a pharmacologically acceptable salt thereof according to the present invention is represented by the following formula:

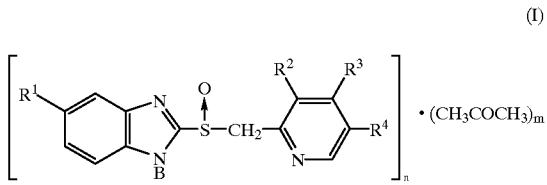

(I)

wherein $R^1$ represents a hydrogen atom, a methoxy group or a difluoromethoxy group, $R^2$ represents a methyl group or a methoxy group, $R^3$ represents a 3-methoxypropoxy group, a methoxy group or a 2,2,2-trifluoroethoxy group, and $R^4$ represents a hydrogen atom or a methyl group;

n represents an integer of 1 to 4, and m represents an integer of 1 to 4, whereupon n and m can vary within the above-described range, depending on reaction conditions such as treatment method, the amount of acetone used, solvent used in combination, treatment temperature, treatment time and stirring rate; and B represents a hydrogen atom, an alkali metal atom or ½alkaline earth metal atom.

In the above definition, the alkali atom includes e.g. sodium atom, potassium atom, lithium atom etc., and the alkaline earthmetal atom includes e.g. calciumatom, magnesium atom etc., among which sodium atom or magnesium atom is more preferable.

The acetone complex (I) of a sulfoxide compound or of a pharmaceutically acceptable salt thereof includes e.g. acetone complex of Rabeprazole, Lansoprazole, Omeprazole or Pantoprazole, or acetone complexes of pharmaceutically acceptable salts thereof.

The acetone complex (I) of a sulfoxide compound or of a pharmaceutically acceptable salt thereof according to the present invention is a novel compound characterized by patterns or absorption peaks in powder X-ray analysis, NMR, IR etc. Further, the acetone complex (I) of a sulfoxide compound or of a pharmaceutically acceptable salt thereof has industrially very superior characters such as stability to conditions such as air, humidity, heat, light, pH etc., thus making the conventionally impossible long-term storage or long-distance transport of the raw material (bulk) possible.

For example, the 2-{[4-(3-methoxypropoxy)-3-methylpyridin-2-yl]methylsulfinyl}-1H-benzimidazole sodium salt acetone complex (II) according to the present invention is specifically characterized in that it has peaks at the following angles expressed in terms of 2θ, in a powder X-ray diffraction pattern (see FIG. 1), and/or peaks at wavelengths of 745.4, 803.1, 1010.2, 1093.0, 1268.1, 1298.5, 1381.4, 1465.2, 1584.5, 1710.6 and 2930.7 cm$^{-1}$ in an infrared absorption spectrum in potassium bromine (see FIG. 2), and/or peaks at δ (ppm) 1.83–2.05 (m, 2H), 2.17 (s, 3H), 3.24 (s, 3H), 3.48 (t, J=6.2 Hz, 2H), 4.09 (t, J=6.2 Hz, 2H), 4.40 (dd, J=13.2 Hz, J=5.7, 1H), 4.72 (dd, J=13.2 Hz, J=5.7, 1H), 6.86 (m, 2H), 6.93 (d, J=5.7, 1H), 7.45 (m, 2H), and 8.27 (d, J=5.7 Hz, 1H) in a $^1$H-NMR (400 MHz, DMSO-d$_6$) spectrum (see FIG. 3).

| Diffractive angles (2θ, °) | Intensity (I/I$_0$) |
|---|---|
| 6.72 | 100 |
| 7.70 | 55 |
| 8.14 | 50 |
| 10.22 | 34 |
| 14.70 | 37 |
| 15.98 | 46 |
| 16.76 | 64 |
| 17.88 | 80 |
| 19.68 | 34 |
| 21.00 | 45 |
| 21.12 | 48 |
| 21.32 | 41 |
| 22.28 | 34 |
| 22.40 | 35 |
| 23.06 | 44 |
| 23.26 | 53 |
| 23.44 | 55 |
| 23.74 | 53 |
| 23.94 | 57 |
| 24.06 | 50 |
| 24.26 | 36 |

Method for Measurement of Powder X-Ray Diffraction Pattern, and Conditions (1) Measurement Method About 100 mg sample was measured for its powder X-ray diffraction pattern under the following measurement conditions.

(2) Measurement Conditions

Target: Cu

Filter: monochro

Voltage: 40 KV

Current: 2 mA

Slit: DS 1; RS 0.15, SS 1

Scan speed: 2 deg/min.

Range: 5–30°

Method for Measurement of IR Absorption Spectrum, and Conditions

Measured in FT-IR in accordance with the Japanese Pharmacopoeia, general test methods, infrared absorption spectrum, and a potassium bromide tablet method.

Next, the sulfoxide compound of the present invention or its pharmacologically acceptable salt (III) is represented by the following formula:

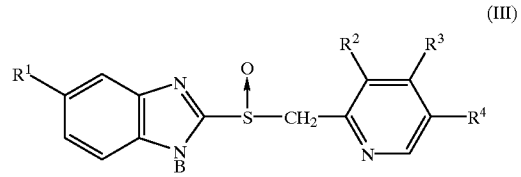

(III)

wherein $R^1$, $R^2$, $R^3$, $R^4$ and B have the same meanings as defined above.

The sulfoxide compound or its pharmacologically acceptable salt (III) is a known compound, and more specifically, mention can be made of 2-{[4-(3-methoxypropoxy)-3-methylpyridin-2-yl]methylsulfinyl}-1H-benzimidazole (general name: Rabeprazole free base) described in JP-A 1-6270 (Example 32), a compound ($R^1$=H, $R^2$=CH$_3$, $R^3$=H, $R^4$=CH$_2$CF$_3$, n=1) (general name, Lansoprazole; chemical name, 2-{[4-(2,2,2-trifluoroethoxy)-3-methylpyridin-2-yl]methylsulfinyl}-1H-benzimidazole) described in JP-A 61-50978 (Example 2), 5-methoxy-2-[(4-methoxy-3,5- dimethyl-2-pyridyl)methylsulfinyl]-1H-benzimidazole (general name: Omeprazole) described in JP-A 54-141783 (Example 21), or 5-difluoromethoxy-2-[(4,5-dimethoxy-2-pyridyl)methylsulfinyl]-1H-benzimidazole (general name: Pantoprazole) described in JP-A 61-22079 etc., or pharmacologically acceptable salts thereof. Any of these compounds can be produced in methods described in the corresponding laid-open publications.

Hereinafter, the process of actually producing the acetone complex (I) of a sulfoxide compound or of a pharmacologically acceptable salt thereof according to the present invention is specifically described.

In the present invention, the acetone complex can be obtained basically by contacting the sulfoxide compound or its pharmacologically acceptable salt (III) with acetone or by dissolving it in acetone and subsequent crystallization thereof. Preferably, the sulfoxide compound or its pharmacologically acceptable salt (III) is dissolved in acetone, and the precipitated acetone complex is filtered and dried.

Further, other solvents may also be used in combination. For example, after the sulfoxide compound or its pharmacologically acceptable salt (III) is treated with acetone, at least one selected from the group consisting of lower hydrocarbons, lower ethers, cyclic ethers, acetonitrile and aromatic hydrocarbons can also be added thereto.

The sulfoxide compound or its pharmacologically acceptable salt (III) can also be treated with acetone in the presence of at least one selected form the group consisting of lower fatty acid esters, lower alcohols, ethers, cyclic ethers, acetonitrile, water, lower hydrocarbons and aromatic hydrocarbons.

Here, the lower hydrocarbons refer to linear or branched hydrocarbons having 5 to 8 carbon atoms, and specific examples include n-pentane, n-hexane, n-heptane, n-octane etc. The lower ethers refer to compounds having a linear or branched alkyl group having 1 to 6 carbon atoms bound symmetrically or unsymmetrically to an oxygen atom, and specific examples include ether, isopropyl ether etc. The cyclic ethers refer to compounds having 4 to 6 carbon atoms, and specific examples include tetrahydrofuran, tetrahydropyran, dioxane, dioxolane etc. The aromatic hydrocarbons refer to benzene compounds, and specific examples include benzene, toluene, xylene, decalin etc. The lower fatty acid esters refer to compounds having a fatty acid having 1 to 6 carbon atoms bound via an ester linkage to a linear or branched alcohol having 1 to 6 carbon atoms, and specific examples include methyl formate, ethyl formate, propyl formate, butyl formate, methyl acetate, ethyl acetate, propyl acetate, butyl acetate, methyl propionate, ethyl propionate, propyl propionate, butyl propionate, methyl butyrate, ethyl butyrate, propyl butyrate, butyl butyrate etc. The lower alcohols refer to linear or branched alcohols having 1 to 6 carbon atoms, and specific examples include methanol, ethanol, isopropanol, butanol etc.

Hereupon, the treatment temperature in the present invention is not limited, and the reaction can be conducted usually at an arbitrary temperature of −20° C. to the boiling point, and good results are given even at room temperature.

The amount of the solvent used is not limited either, and usually, 0.1 to 10 ml acetone, preferably 0.25 to 7.5 ml, more preferably 0.5 to 5 ml is used per g of the sulfoxide compound or its pharmacologically acceptable salt (III). When other solvents are used in combination, their amount and their combination are arbitrarily selected.

The treatment time is not limited either. It is usually 1 to 24 hours which may be varied depending on the treatment method (contacting or dissolution etc.), the amount of acetone used, the type and amount of other solvent used in combination, treatment temperature, stirring rate etc. The precipitated crystals are filtered and dried, whereby the objective acetone complex (I) of the sulfoxide compound or of its pharmacologically acceptable salt can be obtained.

The resulting acetone complex (I) of the sulfoxide compound or of its pharmacologically acceptable salt is converted into an aqueous solution and then lyophilized thereby giving the sulfoxide compound or its pharmacologically acceptable salt useful as medicine such as an inhibitor of gastric acid secretion and an anti-ulcer agent or as an intermediate for production of medicine.

Hereinafter, the present invention is described in more detail by reference to Examples and Reference Examples below, and it is needless to say that they are not intended to limit the present invention.

BRIEF DESCRIPTION OF THE DRAWINGS

FIG. 1 is a powder X-ray diffraction pattern of the 2-{[4-(3-methoxypropoxy)-3-methylpyridin-2-yl]methylsulfinyl}-1H-benzimidazole sodium salt acetone complex (II) obtained in Example 1.

FIG. 2 is an IR chart of complex (II).

FIG. 3 is an NMR chart of complex (II).

EXAMPLES

Example 1 Production of 2-{[4-(3-methoxypropoxy)-3-methylpyridin-2-yl]methylsulyfinyl}-1H-benzimidazole Sodium Salt Acetone Complex

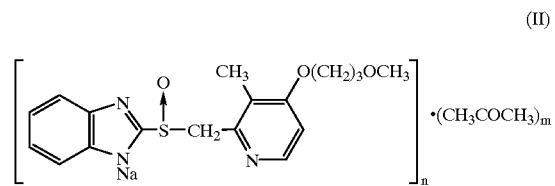

(II)

wherein n and m are independent of each other and represent an integer of 1 to 4.

2-{[4-(3-Methoxypropoxy)-3-methylpyridin-2-yl]methylsulfinyl}-1H-benzimidazole sodium salt (2 g) obtained according to JP-A 1-6270 (Example 33) was dissolved in acetone (3 ml) and left at 4° C. for 24 hours. The precipitated white crystals were filtered and dried to give the title compound.

Example 2 to 4 Production of 2-{[4-(3-methoxypropoxy)-3-methylpyridin-2-yl]methylsulfinyl}-1H-benzimidazole Sodium Salt Acetone Complex The acetone solution was prepared in the same manner as in Example 1 and the following solvent was further added, whereby the title compound was obtained.

| Example No. | Solvent Added | Amount Added |
|---|---|---|
| 2 | n-hexane | 1.5 ml |
| 3 | isopropyl ether | 1.5 ml |
| 4 | toluene | 1.5 ml |

Example 5 Production of 2-{[4-(3-methoxypropoxy)-3-methylpyridin-2-yl]methylsulfinyl}-1H-benzimidazole Sodium Salt Acetone Complex 2-{[4-(3-Methoxypropoxy)-3-methylpyridin-2-yl]methylsulfinyl}-1H-benzimidazole (1.5 g) obtained according to JP-A 1-6270 (Example 32) was dissolved in a mixed solvent of acetone (4.5 ml) and n-heptane (3 ml), and sodium methoxide (225 mg) was added thereto and dissolved in it. The solution was stirred at 5° C. for 12 hours. The precipitated white crystals were filtered and dried to give the title compound (1.46 g).

Example 6 Production of 2-{[4-(3-methoxylpropoxy)-3-methylpyridin-2-yl] methylsulfinyl}-1H-benzimidazole Sodium Salt Acetone Complex 2-{[4-(3-Methoxypropoxy)-3-methylpyridin-2-yl] methylsulfinyl}-1H-benzimidazole sodium salt (7.0 g) was dissolved in ethyl acetate (3 ml), and acetone (3 ml) was added thereto, and the mixture was stirred at 5° C. for 12 hours. The precipitated white crystals were filtered and dried to give the title compound (5.9 g).

Example 7 Production of 2-{[4-(3-methoxypropoxy)-3-methylpyridin-2-yl] methylsulfinyl}-1H-benzimidazole Sodium Salt Acetone Complex 2-{[4-(3-Methoxypropoxy)-3-methylpyridin-2-yl] methylsulfinyl}-1H-benzimidazole sodium salt (10.0 g) was dissolved in acetone (50 ml). After the mixture was stirred at 24° C. for 23 hours, the precipitated white crystals were filtered and washed with acetone (10 ml) The product was dried at 22 20 C. for 20 hours under reduced pressure to give the title compound (11.2 g).

$^1$H-NMR (400 MHz, DMSO-$d_6$); δ (ppm) 1.83–2.05 (m, 2H), 2.17 (s, 3H), 3.24 (s, 3H), 3.48 (t, J=6.2 Hz, 2H), 4.09 (t, J=6.2 Hz, 2H), 4.40 (dd, J=13.2 Hz, J=5.7, 1H), 4.72 (dd, J=13.2 Hz, J=5.7, 1H), 6.86 (m, 2H), 6.93 (d, J=5.7, 1H), 7.45 (m, 2H), and 8.27 (d, J=5.7 Hz, 1H).

Example 8 to 15 Production of 2-{[4-(3-methylpropoxy)-3-methylpyridin-2-yl] methylsulfinyl}-1H-benzimidazole Sodium Salt Acetone Complex Hereinafter, the purification effect (removal of the sulfone compound) according to the present invention is described to show the effect of the present invention.
HPLC Analysis Conditions
Solid phase: NUCLEOSIL$_5$C$_{18}$ (4.6 mm I.D.×150 mm, 5 μm)
Mobile phase: MeOH: 0.05 M phosphate buffer (pH 7)=3:2
Flow rate: 1.0 ml/min.
Temperature: 25° C.
Detector: UV 290 nm

| Example No. | Solvent | Sulfone Content (%) before/after purification | |
|---|---|---|---|
| 8 | ethyl acetate + acetone | 1.19 | 0.67 |
| 9 | THF + acetone | 1.25 | 0.54 |
| 10 | acetonitrile + acetone | 1.25 | 0.52 |
| 11 | water + acetone | 1.75 | 0.30 |
| 12 | methanol + acetone | 1.75 | 0.82 |
| 13 | ethanol + acetone | 1.75 | 0.64 |
| 14 | isopropanol + acetone | 1.75 | 0.74 |
| 15 | t-butanol + acetone | 2.10 | 0.44 |

From the above results, the purification effect of effectively removing the objective sulfone difficult to separate is evident according to the present invention.

The stability of the acetone complex (I) of a sulfoxide compound or of a pharmaceutically acceptable salt thereof according to the present invention makes conventionally impossible long-term storage or long-distance transport of the raw material (bulk) possible, to attain industrially very excellent characters.

Reference Example 1 Production of 2-{[4-(3-methoxypropoxy)-3-methylpyridin-2-yl] methylsulfinyl}-1H-benzimidazole Sodium Salt After the acetone complex (10.0 g) obtained in Example 7 was dissolved in distilled water (20 ml), it was frozen in a dry ice/methanol bath. It was then lyophilized for 48 hours to give the amorphous title compound (8.8 g) (yield: quantitative).

What is claimed is:
1. An acetone complex of 2-{(4-(3-Methoxypropoxy)-3-methylpyridin-2-yl) methylsulfinyl}-1H-benzimidazole•sodium salt•acetone complex (II) represented by the following chemical formula:

(II)

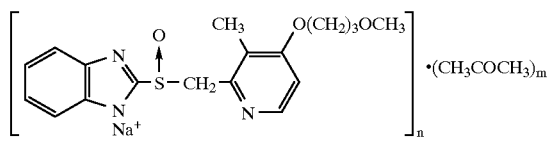

wherein
n represents an integer of 1 to 4; and
m represents an integer of 1 to 4, the complex having peaks at the following diffractive angles expressed in terms of 2$^θ$, in a powder X-ray diffraction pattern,

| Diffractive angles (2$^θ$, °) | Intensity (I/I$_0$) |
|---|---|
| 6.72 | 100 |
| 7.70 | 55 |
| 8.14 | 50 |
| 10.22 | 34 |
| 14.70 | 37 |
| 15.98 | 46 |
| 16.76 | 64 |
| 17.88 | 80 |
| 19.68 | 34 |
| 21.00 | 45 |
| 21.12 | 48 |
| 21.32 | 41 |
| 22.28 | 34 |
| 22.40 | 35 |
| 23.06 | 44 |
| 23.26 | 53 |
| 23.44 | 55 |
| 23.74 | 53 |
| 23.94 | 57 |
| 24.06 | 50 |
| 24.26 | 36. | and/or peaks at wavelengths of 745.4, 803.1, 1010.2, 1093.0, 1268.1, 1298.5, 1381.4, 1465.2, 1584.5, 1710.6 and 2930.7 cm$^{-1}$ in an infrared absorption spectrum in potassium bromine, and/or peaks at δ (ppm) 1.83–2.05 (m, 2H), 2.17 (s, 3H), 3.24 (s, 3H), 3.48 (t, J=6.2 Hz, 2H), 4.09 (t, J=6.2 Hz, 2H), 4.40 (dd, J=13.2 Hz, J=5.7, 1H), 4.72 (dd, J=13.2 Hz, J=5.7, 1H), 6.86 (m, 2H), 6.93 (d, J=5.7, 1H), 7.45 (m, 2H), and 8.27 (d, J=5.7 Hz, 1H) in a $^1$H-NMR (400 MHz, DMSO-$d_6$) spectrum.

2. A process for producing the acetone complex (II) as claimed in claim 1, or a pharmaceutically acceptable salt thereof, wherein the compound represented by the following formula:

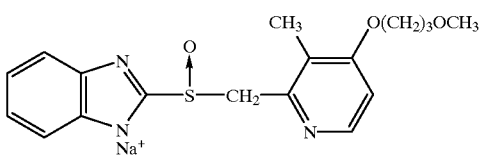

or its pharmacologically acceptable salt is treated with acetone.

3. The process as claimed in claim 2, which comprises the steps of treating the compound or its pharmacologically acceptable salt with acetone and adding at least one group selected from lower hydrocarbons, lower ethers, cyclic ethers, acetonitrile and aromatic hydrocarbons thereto to produce acetone complex (II) of a sulfoxide compound or of a pharmaceutically acceptable thereof.

4. The process as claimed in claim 2, wherein the compound or its pharmacologically acceptable salt is treated with acetone in the presence of at least one group selected from the group consisting of lower fatty acid esters, lower alcohols, ethers, cyclic ethers, acetonitrile, water, lower hydrocarbons and aromatic hydrocarbons to produce acetone complex (II) of a sulfoxide compound or of a pharmaceutically acceptable salt thereof.

5. The process as claimed in claim 2, wherein the compound or its pharmacologically acceptable salt is treated with acetone in the presence of at least one group selected from the group consisting of ethyl acetate, methanol, ethanol, isopropanol, butanol, tetrahydrofuran, acetonitrile, water, n-hexane, n-heptane and toluene to produce acetone complex (II) of a sulfoxide compound or of a pharmaceutically acceptable salt thereof.

6. The process as claimed in claim 2, wherein 2-{[4-(3-methoxypropoxy)-3-methylpyridin-2-yl]methylsulfinyl}-1H-benzimidazole sodium salt is treated with acetone to produce an acetone complex of 2-{[4-(3-methoxypropoxy)-3-methylpyridin-2-yl]methylsulfinyl}-1H-benzimidazole sodium salt.

7. The process as claimed in claim 2, which comprises the steps of treating 2-{[4-(3-methoxypropoxy)-3-methylpyridin-2-yl]methylsulfinyl}-1H-benzimidazole sodium salt with acetone and adding at least one group selected from the group consisting of lower hydrocarbons, lower ethers and aromatic hydrocarbons thereto to produce an acetone complex of 2-{[4-(3-methoxypropoxy)-3-methylpyridin-2-yl]methylsulfinyl}-1H-benzimidazole sodium salt.

8. A process for producing a sulfoxide compound or its pharmaceutically acceptable salt, as defined in claim 2, wherein an aqueous solution of the acetone complex (II) of a sulfoxide compound or of a pharmaceutically acceptable salt thereof, as defined in claim 1, is lyophilized.

9. The process as claimed in claim 8, wherein an aqueous solution of 2-{[4-(3-methoxypropoxy)-3-methylpyridin-2-yl]methylsulfinyl}-1H-benzimidazole sodium salt acetone complex (II) is lyophilized to produce 2-{[4-(3-methoxypropoxy)-3-methylpyridin-2-yl]methylsulfinyl}-1H-benzimidazole sodium salt.

* * * * *